(12) United States Patent
Schetz et al.

(10) Patent No.: US 9,192,598 B2
(45) Date of Patent: *Nov. 24, 2015

(54) PREVENTION OF BACTERIAL GROWTH AND BIOFILM FORMATION BY LIGANDS THAT ACT ON CANNABINOIDERGIC SYSTEMS

(75) Inventors: John A. Schetz, Fort Worth, TX (US); Sally A. Hoger, Fort Worth, TX (US)

(73) Assignees: University of North Texas Health Science Center at Fort Worth, Fort Worth, TX (US); The Texas A&M University System, College Station, TX (US)

( * ) Notice: Subject to any disclaimer, the term of this patent is extended or adjusted under 35 U.S.C. 154(b) by 761 days.

This patent is subject to a terminal disclaimer.

(21) Appl. No.: 13/000,147

(22) PCT Filed: Jun. 25, 2009

(86) PCT No.: PCT/US2009/048660
§ 371 (c)(1),
(2), (4) Date: Aug. 23, 2011

(87) PCT Pub. No.: WO2009/158499
PCT Pub. Date: Dec. 30, 2009

(65) Prior Publication Data
US 2011/0301078 A1  Dec. 8, 2011

Related U.S. Application Data

(60) Provisional application No. 61/133,096, filed on Jun. 25, 2008.

(51) Int. Cl.
| | |
|---|---|
| A01N 37/18 | (2006.01) |
| A61K 38/00 | (2006.01) |
| A61P 31/04 | (2006.01) |
| A61K 38/04 | (2006.01) |
| A01N 43/00 | (2006.01) |
| A61K 31/33 | (2006.01) |
| A01N 55/02 | (2006.01) |
| A61K 31/555 | (2006.01) |
| A01N 43/16 | (2006.01) |
| A61K 31/35 | (2006.01) |
| A01N 41/06 | (2006.01) |
| A61K 31/18 | (2006.01) |
| A61K 31/16 | (2006.01) |
| A01N 33/02 | (2006.01) |
| A61K 31/135 | (2006.01) |
| A01N 31/00 | (2006.01) |
| A61K 31/045 | (2006.01) |
| A01N 33/24 | (2006.01) |
| A61K 31/04 | (2006.01) |
| A01N 27/00 | (2006.01) |
| A61K 31/015 | (2006.01) |
| A61K 31/352 | (2006.01) |
| A01N 31/02 | (2006.01) |
| A01N 31/08 | (2006.01) |
| A01N 37/20 | (2006.01) |
| A61K 31/05 | (2006.01) |
| A61K 31/08 | (2006.01) |
| A61K 31/164 | (2006.01) |
| A61K 45/06 | (2006.01) |
| A61L 15/44 | (2006.01) |

(52) U.S. Cl.
CPC .............. *A61K 31/352* (2013.01); *A01N 31/02* (2013.01); *A01N 31/08* (2013.01); *A01N 37/20* (2013.01); *A01N 43/16* (2013.01); *A61K 31/05* (2013.01); *A61K 31/08* (2013.01); *A61K 31/16* (2013.01); *A61K 31/164* (2013.01); *A61K 31/18* (2013.01); *A61K 31/35* (2013.01); *A61K 38/00* (2013.01); *A61K 45/06* (2013.01); *A61L 15/44* (2013.01); *A61L 2300/30* (2013.01); *A61L 2300/404* (2013.01); *A61L 2300/406* (2013.01); *A61L 2300/45* (2013.01)

(58) Field of Classification Search
None
See application file for complete search history.

(56) References Cited

U.S. PATENT DOCUMENTS

| 8,575,230 B2 * | 11/2013 | Schetz et al. .................. 523/122 |
| 2010/0256256 A1 * | 10/2010 | Schetz et al. .................. 523/122 |

FOREIGN PATENT DOCUMENTS

WO   WO 2008130558 A2 * 10/2008 ............... C09D 5/16

OTHER PUBLICATIONS

Cabral, et al., "Cannabinoid-mediated Inhibition of Inducible Nitric Oxide Production by Rat Microglial Cells: Evidence for CB1 Receptor Participation," Adv. Exp. Med. Biol. 493:207-214 (2001).*

(Continued)

*Primary Examiner* — James H Alstrum Acevedo
*Assistant Examiner* — Thea D'Ambrosio
(74) *Attorney, Agent, or Firm* — Jackson Walker L.L.P.

(57) ABSTRACT

A group of antimicrobial compounds shows effectiveness for preventing bacterial growth and bio film formation. In particular, the compounds are effective for preventing the growth of gram-positive bacteria, including methicillin-resistant *Staphylococcus aureus* ("MRSA") bacteria. The compounds include naturally-occurring compounds such as linoleyl ethanolamide, noladin ether, and anandamide, and man-made compounds such as CP55,640 [(−)-cis-3-[2-Hydroxy-4-(1,1-dimethylheptyl)phenyl]-trans-4-(3-hydroxypropyl)cyclohexanol] and O-2050 [(6aR,10aR)-3-(1-Methanesulfonylamino-4-hexyn-6-yl)-6a,7,10,10a-tetrahydro-6,6,9-trimethyl-6H-dibenzo[b,d]pyran]. Because these antibacterial compounds have unique modes of action and/or unique chemical scaffolds compared to traditional antibiotics, they are extremely useful against bacteria having resistances to antibiotics.

7 Claims, 4 Drawing Sheets

(56) References Cited

OTHER PUBLICATIONS

Fujimori et al., "Increase in Serum Cannabinoids in a Rat Model of Septic Shock Induced by the Cell Wall Components of *Staphylococcus aureus*," Showa Univeristy J. of Medical Science 14:135-142 (2002).*

Gross, et al "A beneficial aspect of a CB1 cannabinoid receptor antagonist: SP141716A is a potent inhibitor of macrophase infection by the intracellular pathogen Brucella suis," J. Leukocyte Biol. 67:335-344 (2000).*

Van Klingeren et al., "Antibacterial activty of delta9-tetrahydrocannabinol and cannabidiol," Antonie van Leeuwenhoek 42:9-12 (1976).*

U.S. Appl. No. 14/063,568, filed Oct. 2013, Schetz.*

Abee, et al., "Biofilm formation and dispersal in Gram-positive bacteria," Curr. Opin. Biotechnol. 22:172-179 (2011).*

Fitridge et al., "The impact and control of biofouling in marine aquaculture: a review," Biofouling 28:649-669 (2012).*

Kiedrowski et al., "New approaches for treating staphylococcal biofilm infections," Ann. NY Acad. Sci. 1241:104-121 (2011).*

Simoes, et al., "A review of current and emergent biofilm control strategies," Food Sci. Technol. 43:573-583 (2010).*

Fujimori et al., Showa Univ. J. Med. Sci. 14:135-142 (2002).*

Ahmed, Safwat A., et al; Cannabinoid Ester Constituents From High-Potency Cannabis Sativa; J. Nat. Prod., 71, 536-542, Feb. 28, 2008.

Appendino, Giovanni, et al; Antibacterial Cannabinoids From Cannabis Sativa: A Structure-Activity Study; J. Nat. Prod., 71, 1427-1430, Aug. 6, 2008.

Radwan, Mohamed M., et al; Biologically Active Cannabinoids From High-Potency Cannabis Sativa; J. Nat. Prod., 72, 906-911, Apr. 3, 2009.

* cited by examiner

Figure 1

| Cmp No. | Chemical Name | Chemical Structure |
|---|---|---|
| 2 | Anandamide<br>CAS: 94421-68-8<br>MW: 347.6<br>Sigma No: A0580<br>*Note: also called arachidonylethanolamide* | 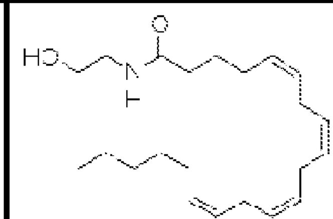 |
| 17 | Linoleyl ethanolamide<br>CAS: 68171-52-8<br>MW: 323.5<br>Sigma No: L1164<br>*Note: alternate spelling is linoleoyl ethanolamide* | 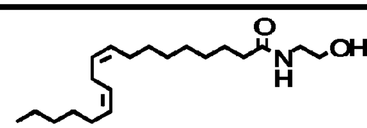 |
| 21 | O-2050<br>CAS: 667419-91-2<br>MW: 417.56<br>Tocris No: 1655 | 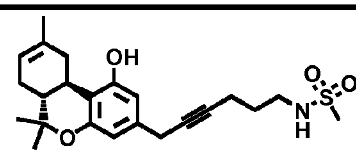 |
| 22 | Noladin ether<br>CAS: 222723-55-9<br>MW: 364.6<br>Tocris No: 1411 | 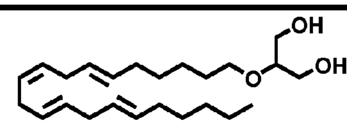 |
| 23 | CP 55,940<br>CAS: 83002-04-4<br>MW: 376.6<br>Tocris No: 0949 | 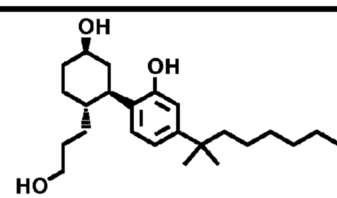 |

PREVENTION OF BACTERIAL GROWTH AND BIOFILM FORMATION BY LIGANDS THAT ACT ON CANNABINOIDERGIC SYSTEMS

This application claims priority to U.S. Provisional Patent Application Ser. No. 61/133,096, entitled "Prevention of Bacterial Growth and Biofilm Formation By Ligands That Act on Cannabinoidergic Systems," filed on Jun. 25, 2008, the entire content of which is hereby incorporated by reference.

BACKGROUND

This invention relates to the formulation and method of using an effective amount of a compound, or ligand, or chemical agent, that acts on cannabinoidergic systems, or a mixture containing the compound, optionally combined with a carrier, to effectively inhibit the growth of bacteria, the formation of biofilm, or both.

In the United States, drug-resistant bacteria are the leading cause of death due to infection. In fact, the number of annual deaths due to common drug-resistant bacteria surpasses those due to smoking and tobacco. *Staphylococcus aureus* bacteria infections are the source of a number of potentially lethal diseases affecting skin, lung, and blood and whose courses and symptoms depend upon the tissue that becomes infected. While skin infections, including sites of surgery, are quite common and sometimes deadly, the most lethal, and for this reason the best known, are pneumonia due to infection of the lungs or severe sepsis (septic shock) due to infection of the blood. Resistance to antibiotics is a cause for major concern for a number of infectious bacterial strains, and chief amongst them is methicillin-resistant *Staphylococcus aureus*.

Methicillin-resistant *Staphylococcus aureus* ("MRSA") strains account for most hospital-acquired and nursing home-acquired infections and they are a leading cause of mortality due to infection. They are also a leading cause of close quarter community-acquired infections impacting children in day-care centers, members of sports teams, military personnel, and prisoners. The instances of serious MRSA infection in the US has mushroomed in the past decade to the point where the rate of invasive MRSA exceeds the combined rate of invasive infections due to pneumococcal disease, meningococcal disease, group A *streptococcus*, and *Haemophilus influenza*. While overall incidents of MRSA are relatively low, the risk of death from an MRSA infection is very high, as is the cost associated with treatment.

As the infection rate increases, there have actually been fewer unique classes of drugs introduced to combat these infections. Given that only two new antibiotic pharmacophores have been introduced into the clinic over the last 30 plus years (Barrett 2003; Pucci 2006) locating structurally and/or mechanistically novel antimicrobial approaches is of considerable interest. This is especially true given that antibiotic resistance is on the rise (Levy 2004) and the fact that large drug companies are increasingly less interested in supporting antimicrobial discovery programs (Projan 2003). Innovative ways to prevent MRSA infections are clearly needed.

Lipophilic fractions isolated from leaves of *Cannabis sativa* have been shown to have antimicrobial activity (Wasim 1995). Isolated components of *Cannabis*, such as cannabichromene, cannabigeral, and cannabidiol and delta-9-THC, have also been reported to have antimicrobial activity (Van Klingeren 1976; Turner 1981; Elsohly 1982).

SUMMARY

The present invention relates generally to a formulation and a method of using an effective amount of a compound, or ligand, or chemical agent, that acts on cannabinoidergic systems, or a mixture containing the compound, optionally combined with a carrier, to effectively inhibit the growth of bacteria, the formation of biofilm, or both. In particular, the compounds, or ligand, or chemical agents, include cannabinoids and in particular include those cannabinoids that are effective against gram-positive bacteria, including MRSA. Examples of those compounds include CP55,940 [(−)-cis-3-[2-Hydroxy-4-(1,1-dimethylheptyl)phenyl]-trans-4-(3-hydroxypropyl)cyclohexanol], linoleoyl ethanolamide ("LEA") [N-(2-hydroxyethyl)-9Z,12Z-octadecadienamide], also spelled linoleyl ethanolamide, O-2050 [(6aR,10aR)-3-(1-Methanesulfonylamino-4-hexyn-6-yl)-6a,7,10,10a-tetrahydro-6,6,9-trimethyl-6H-dibenzo[b,d]pyran], noladin ether [2-[(5Z,8Z,11Z,14Z)-eicosatetraenyloxy]-1,3-propanediol], and anandamide[N-(2-Hydroxyethyl)-5Z,8Z,11Z,14Z-eicosatetraenamide], all of which are pictured in the table below.

CP 55,940
(CAS: 83002-04-4)

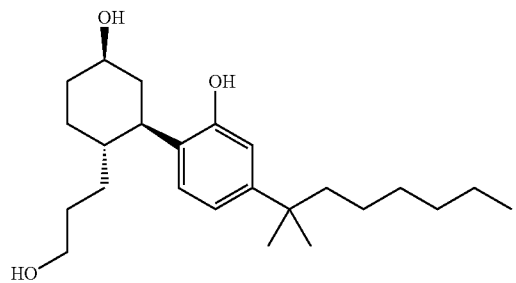 [SMILES: CCCCCCC(C)(C)c1ccc([C@@H]2C[C@H](O)CC[C@H]2CCCO)c(O)c1]

Linoleoyl ethanolamide ("LEA")
(CAS: 68171-52-8)

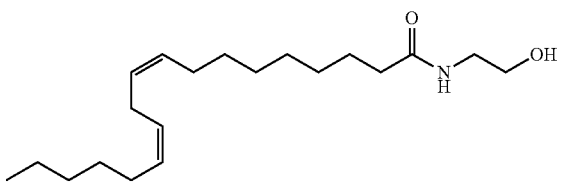

O-2050
(CAS: 667419-91-2)

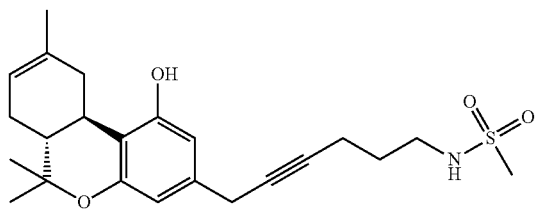 [SMILES: CC1=CC[C@@H]2[C@@H](C1)c1c(O)cc(CC#CCCCNS(C)(=O)=O)cc1OC2(C)C]

Noladin ether
(CAS: 222723-55-9)

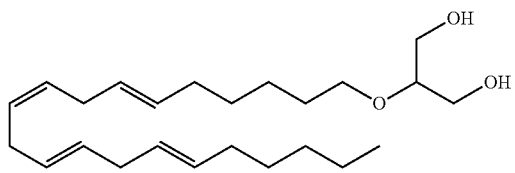 [SMILES: CCCCC/C=C/C/C=C/C/C=C\C/C=C/CCCCCOC(CO)CO]

Anandamide
(CAS: 94421-68-8)

-continued

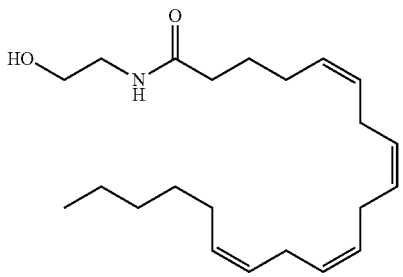

By means of illustration only, and without being bound by theory, CP 55,940 is a high affinity and high efficacy CB1 and CB2 agonist, as well as a GPR55 receptor agonist, with a THC-like structure. LEA is a structurally distinct endogenous cannabinoid and indirect agonist. LEA has poor affinity for mammalian CB1 and CB2 receptors, but it is an inhibitor of fatty acid amide hydrolase ("FAAH"), an enzyme responsible for degradation of the endocannabinoid agonist anandamide (Maurelli 1995; Maccarrone 1998). Noladin ether is also mammalian CB1 receptor agonists, while O-2050 is reported to be a mammalian CB1 receptor antagonist.

The current antibacterial compounds are all effective for preventing MRSA growth and biofilm formation and are structurally unique for antimicrobials. Without wanting to be bound by theory, as the current antibacterial compounds are mammalian ligands for cannabinoid receptors or cannabinoid metabolic enzymes, their mode of action is also unique. Noladin ether, anandamide, and LEA are natural products and putative endocannabinoids. Any of these compounds could be added to a topical treatment, such as ointments, lotions, creams or sprays, or to an anti-infective coating applied to a medical device, such as catheters, hemodialysis equipment, pulmonary ventilators, heart valves, dialysis equipment, and surgical equipment. Due to their structural uniqueness and/or their unique modes of action, these compounds are particularly useful against bacteria having resistances to traditional antibiotics.

BRIEF DESCRIPTION OF THE DRAWINGS

FIG. 1 shows the structures and additional information for a set of antibacterial compounds.

DETAILED DESCRIPTION OF PREFERRED EMBODIMENTS

Figure 2:
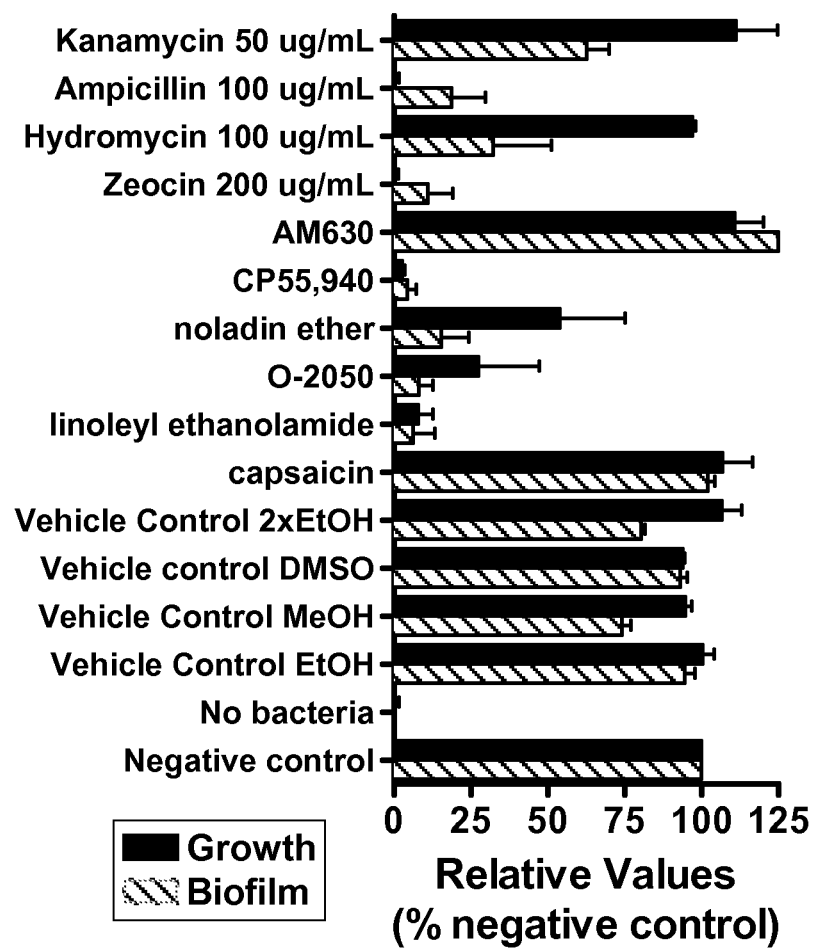
FIG. 2 shows the results of a bacterial and biofilm growth study showing the effectiveness of a set of antibacterial compounds.

The methods described herein involve the use of compounds, or ligands, or chemical agents, that act on cannabinoidergic systems, or their mixtures, alone or combined with carriers, to effectively inhibit the growth of bacteria, inhibit the formation of biofilm, or both. For example, this would include compounds that interact with cannabinoid receptors or enzymes involved in the metabolism of cannabinoids or transporters involved in the transport of cannabinoids. In particular, the methods are effective against the growth of gram-positive bacteria, including MRSA. The compounds include the cannabinoid receptor ligands CP55,940 [(−)-cis-3-[2-Hydroxy-4-(1,1-dimethylheptyl)phenyl]-trans-4-(3-hydroxypropyl)cyclohexanol], linoleoyl ethanolamide ("LEA") [N-(2-hydroxyethyl)-9Z,12Z-octadecadienamide], also spelled linoleyl ethanolamide, O-2050 [(6aR,10aR)-3-(1-Methanesulfonylamino-4-hexyn-6-yl)-6a,7,10,10a-tetrahydro-6,6,9-trimethyl-6H-dibenzo[b,d]pyran], noladin ether [2-[(5Z,8Z,11Z,14Z)-eicosatetraenyloxy]-1,3-propanediol], and anandamide[N-(2-Hydroxyethyl)-5Z,8Z,11Z,14Z-eicosatetraenamide]. FIG. 1 shows the structures, Chemical Abstracts Services ("CAS") registration numbers and some additional details about the antibacterial compounds.

A first compound having antibacterial activity that is also effective against biofilm formation is linoleoyl ethanolamide ("LEA"), having the structure shown below:

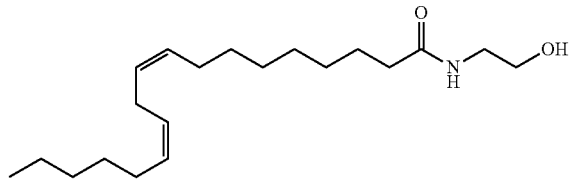 [SMILES: CCCCC/C=C\C/C=C\CCCCCCCC(=O)NCCO]

An additional compound having antibacterial activity that is also effective against biofilm formation is O-2050, having the structure shown below:

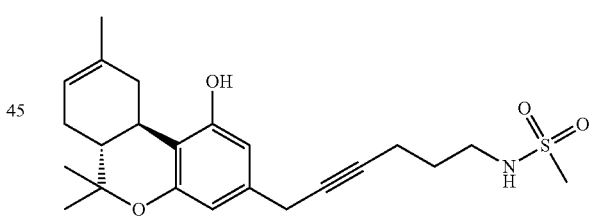

An additional compound having antibacterial activity that is also effective against biofilm formation is noladin ether, having the structure shown below:

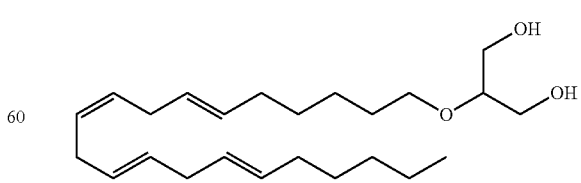

An additional compound having antibacterial activity that is also effective against biofilm formation is CP55,940, having the structure shown below:

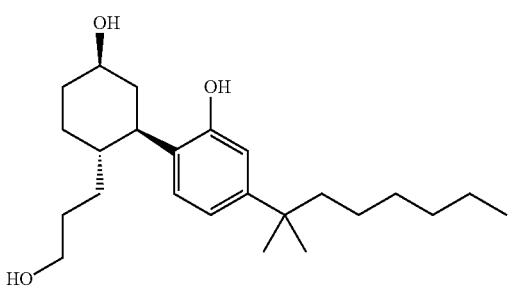 [SMILES: CCCCCCC(C)(C)c1ccc([C@@H]2C[C@H](O)CC[C@H]2CCCO)c(O)c1]

An additional compound having antibacterial activity that is also effective against biofilm formation is anandamide, also called AEA or arachidonylethanolamine, having the structure shown below:

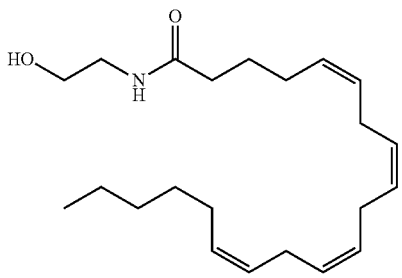 [SMILES: CCCCC/C=C\C/C=C\C/C=C\C/C=C\CCCC(=O)NCCO]

The current compounds are useful as antibacterial agents and useful in the prevention of the formation of biofilms, and particularly as agents against gram-positive bacteria, including MRSA. An effective amount of the compound or combinations thereof could be mixed with a suitable carrier and used as anti-infective topical applications, such as creams, lotions, ointments or sprays that could be made with or without other established antibiotics, belonging to the structural classes of amino glycoside, cephalosphorins, beta-lactams, penicillins, sulfonamides, tetracyclines, quinolones, fluoroquinolones, glycopeptide, lipopeptide, macrolides, monobactams, ansamycins, carbacephem and/or including specific antibiotics such as neomycin, bacitracin, polymyxin B, clindamycin, erythromycin, streptomycin, kanamycin, gentamicin, tetracycline, sulfacetamide, metronidazole, mupirocin, retinol, adapalene, tazarotene, tretinoin, isotretinoin, benzoyl peroxide, azelaic acid, salicylic acid, REP8839 (Replidyne, Inc., Louisville, Colo.), vancomycin, daptomycin, linezolid, trimethoprim-sulfamethoxazole, minocycline, doxycycline, trovafloxacin, levofloxacin, ciprofloxacin, nalidixic acid, azithromycin, quinupristin/dalfopristin, rifampin, rifampicin, nitrofurantoin, isoniazid, pyrazinamide, tinidazole, platensimycin, chloramphenicol, fusidic acid, furazolidone, lincomycin, ethambutol, fosfomycin, arsphenamine, mafenide, colistin, clarithromycin or mixtures thereof. As used herein, "an effective amount" or "an effective amount of a cannabinoidergic-system-acting compound" means that amount which will provide the desired interaction with cannabinoid receptors, the desired involvement with the metabolism of cannabinoids, or the desired involvement with the transport of cannabinoids to give a discernable effect of inhibiting the growth of bacteria, inhibiting the formation of biofilm, or both. For example, an effective dose might be one that reduces bacterial growth and/or biofilm formation by at least 70% for a lower starting concentration of bacterial (e.g., ca 5000 CFU/mL, see FIG. 2) or by at least 30% for a higher starting concentration of bacteria (e.g., ca 50,000 CFU/mL). In addition to antibiotics, the anti-infective topical applications can also contain any suitable adjuvants, preferably those that are known to assist in wound healing, such as aloe, zinc oxide, grapeseed oil, or combinations of these.

In addition, these compounds could be used in anti-infective coatings applied to various medical devices, including catheters, hemodialysis equipment, pulmonary ventilators, heart valves, dialysis equipment, and surgical equipment. These compounds could also be impregnated into bandages or other wound dressing materials. The wound dressing materials treated with the compounds would then have anti-infective properties. It is also possible that these compounds could be administered as drugs, either oral, sublingual, as eye, nose, or ear drops, or as an injection or inhalant. These uses are in addition to traditional uses as a systemic antibiotic, and other uses within the scope of this invention may be apparent as well.

These compounds are extremely beneficial in uses against drug-resistant bacteria because, among other things, their structures are unique and have not been previously used against bacteria. Thus, bacteria have not developed a resistance to them. Furthermore, some of the compounds include natural products, which potentially lowers any barriers to market entry.

Example 1

The broth inoculum was prepared from 18-24 hours old colonies grown on standard agar plates. Approximately four of the fresh colonies were swiped with a sterile cotton Q-tip and then suspended in saline by immersion and light swirling. The turbidity was adjusted to equal that of a 0.5 McFarland turbidity standard using a spectrophotometer (600 nm). The amount corresponded to about $1.5 \times 10^8$ CFU/mL, where CFU stands for colony-forming units, and is equivalent to an absorbance at 600 nm equal to 0.132 or a percentage transmission equal to 74.3. A 1:15,000 v/v final dilution into two mL of commercially-available quality-control-tested bacterial culture Mueller-Hinton Broth resulted in broth inoculated with approximately $5 \times 10^3$ bacteria. Sterile 4 mL polystyrene tubes (12×75 mm) with caps were used for this purpose.

MRSA bacteria (about 5000 CFU/mL) were allowed to grow for 16-20 hours in 2 mL broth at 35±2° C. in the presence or absence of various experimental compounds or antibiotics. The amount of biofilm was visualized qualitatively after being stained with crystal violet. Biofilm attached to the side of the tube was stained purple. The compounds CP55,940, LEA, and capsaicin were all tested at 30 μm. The results are shown in FIG. 2. In the negative control, no compounds were added. The vehicle controls were made up of the appropriate dilution of the different solvent used to dissolve the experimental compounds, including methanol (MeOH), ethanol (EtOH) or dimethylsulfoxide (DMSO). The experimental compounds tested included CP55,940, noladin ether, O-2050, and linoleyl ethanolamide. High concentrations of the antibiotics zeocin and ampicillin served as positive antimicrobial controls. Relatively ineffective antibiotics Hydromycin B and kanamycin were also tested. The no bacteria group contained only media and no bacteria, and served as another control. The results show that both natural (i.e., LEA and noladin ether) and man-made (i.e., CP55,940 and O-2050) compounds prevent MRSA growth and biofilm formation.

Example 2

The efficacy of the compounds were again tested against different strains of gram-positive bacteria, including *Strepto-*

*coccus agalactiae, Enterococcus faecalis, Staphylococcus epidermidis*, and prominent MRSA (hospital-acquired and community-acquired) strains. Broth inoculum was prepared from 18-24 hours old colonies grown on standard agar plates. Approximately four of the fresh colonies were swiped with a sterile cotton Q-tip and then suspended in saline by immersion and light swirling. The turbidity was adjusted to equal that of a 0.5 McFarland turbidity standard using a spectrophotometer (600 nm). The amount corresponded to about $1.5 \times 10^8$ CFU/mL, where CFU stands for colony-forming units, and is equivalent to an absorbance at 600 nm equal to 0.132 or a percentage transmission equal to 74.3. A 1:15,000 v/v final dilution into two mL of commercially-available quality-control-tested bacterial culture Mueller-Hinton Broth resulted in broth inoculated with approximately $5 \times 10^3$ bacteria. Sterile 4 mL polystyrene tubes (12×75 mm) with caps were used for this purpose.

Figure 3:
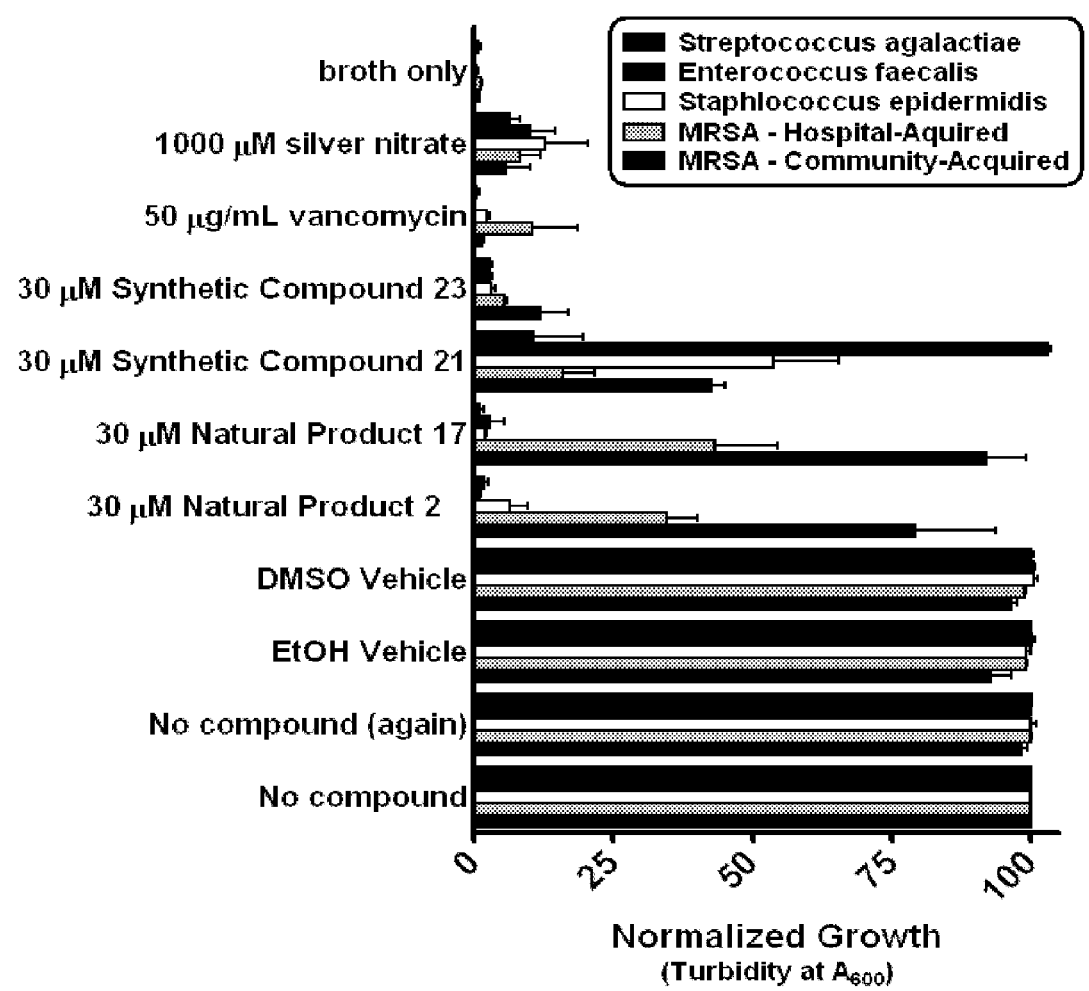
FIG. 3 shows the results of a bacterial and biofilm growth study showing the effectiveness of a set of antibacterial compounds.

The bacteria were allowed to incubate overnight in 2 mL broth at 35±2° C. in the presence or absence of various experimental compounds or antibiotics. The amount of biofilm was visualized qualitatively, then stained with crystal violet. Biofilm attached to the side of the tube was stained purple. After staining, the tubes were decanted and rinsed, leaving stained biofilm adhering to the tubes. Next, the stain was solubilized and mixed with ethanol (EtOH) or dimethylsulfoxide (DMSO). The turbidity of the so lubilized stain, or lack thereof, was then quantified in a spectrophotometer (600 nm). The results are shown in FIG. 3. In the broth only sample, no bacteria were added. In the negative controls, no compounds were added. The vehicle controls were made up of the appropriate dilution of the different solvent used to dissolve the experimental compounds, including ethanol (EtOH) or dimethylsulfoxide (DMSO). The experimental compounds tested included 30 µM of CP55,940, 30 µM of O-2050, 30 µM of linoleyl ethanolamide, 30 µM of no ladin ether, and 30 µM of anandamide (natural product 2). High concentrations of silver nitrate (1000 µM) and vancomycin (50 µg/mL) served as positive antimicrobial controls. The results show that both natural (i.e., LEA) and man-made (i.e., CP55,940 and O-2050) compounds prevent growth of gram-positive bacteria, including MRSA, and biofilm formation.

Example 3

Figure 4:
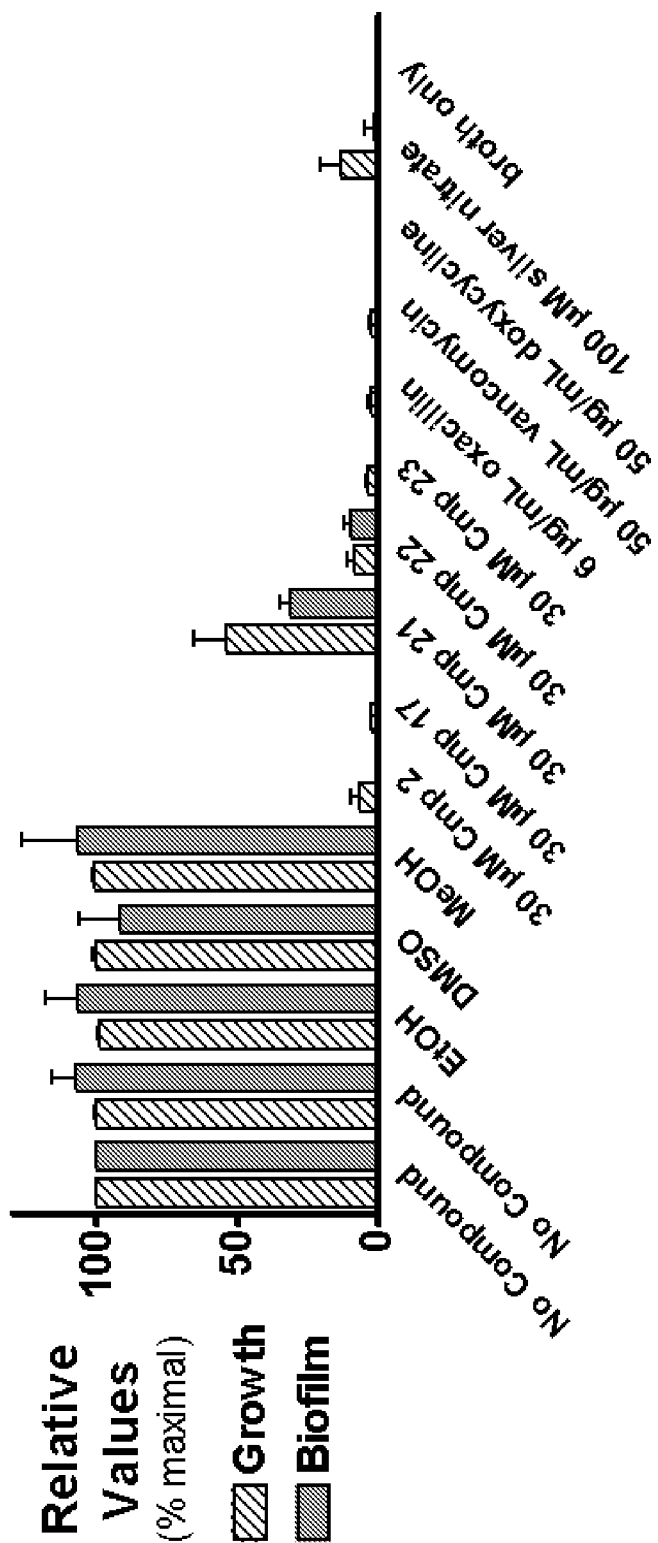
FIG. 4 shows the results of a bacterial and biofilm growth study showing the effectiveness of a set of antibacterial compounds.

In this example, the same procedure was followed as in Example 1, but the bacterial growth and biofilm formation measured was from *Staphylococcus epidermidis*. The experimental compounds included Compound 2 (anandamide), Compound 17 (linoleyl ethanolamide), Compound 21 (O-2050), Compound 22 (noladin ether), and Compound 23 (CP55,940), all at 30 µM. In the negative control, no compounds were added. The vehicle controls were made up of the appropriate dilution of the different solvent used to dissolve the experimental compounds, including methanol (MeOH), ethanol (EtOH) or dimethylsulfoxide (DMSO). High concentrations of the antibiotics oxacillin (6 µg/mL), vancomycin (50 µg/mL), doxycycline (50 µg/mL), and silver nitrate (100 µM) served as positive antimicrobial controls. The broth only sample contained only media and no bacteria, and served as another control. The results, shown in FIG. 4, demonstrate that the same experimental compounds that inhibit MRSA growth and biofilm formation also inhibit *S. epidermidis* growth and biofilm formation.

REFERENCES CITED

The following U.S. Patent documents and publications are hereby incorporated by reference.

U.S. Patent Documents

U.S. Provisional Patent Application No. 60/925,260

Other Publications

Barrett C. T., Barrett J. F., Antibacterials: are the new entries enough to deal with the emerging resistance problems? *Curr Opin Biotechnol.* 2003 December, 14(6):621-626.

ElSohly, H. N., C. E. Turner, A. M. Clark, and M. A. ElSohly, Synthesis and antimicrobial activity of certain cannabichromene and cannabigerol related compounds. *Journal of Pharmaceutical Sciences* 1982, 71: 1319-1323.

Levy, S. B., Marshall, B. Antibacterial resistance worldwide: causes, challenges and responses. *Nat. Med.* 10 (12 Suppl): S122-129 (2004).

Maccarrone, M., Vander Stelt, M., Rossi, A., Veldink, G. A., Vliegenthart, J. F. and Agro, A. F. Anandamide hydrolysis by human cells in culture and brain. *J. Biol. Chem.*, 273, 32332-32339 (1998).

Maurelli, S., Bisogno, T., De Petrocellis, L., Diluccia, A., Marino, G. and Di Marzo, V. Two novel classes of neuroactive fatty acid amides are substrates for mouse neuroblastoma 'anandamide amidohydrolase'. *Febs Lett.*, 377, 82-86 (1995).

Projan, S. J. Why is big Pharma getting out of antibacterial drug discovery? *Curr Opin Microbiol.* 6:427-430 (2003).

Pucci, M. J. Use of genomics to select antibacterial targets. *Biochem Pharmacol.* 71:1066-1072 (2006).

Turner, C. E., Elsohly, M. A., Biological activity of cannabichromene, its homologs and isomers. *Journal of Clinical Pharmacology* 1981, 21(8-9 Suppl), 283S-291S.

Van Klingeren, B. and M. Ten Ham, Antibacterial activity of delta-9-THC and cannabidiol. *Antonie van Leeuwenhoek Journal of Microbiology and Serology* 1976 42: 9-12.

Wasim, K., Haq, I., Ashraf, M. Antimicrobial studies of the leaf of *cannabis sativa* L. *Pak J Pharm Sci.* 1995; 8:29-38.

What is claimed is:

1. A method of inhibiting or reducing gram positive bacterial growth or gram positive bacterial biofilm formation on a surface in need of an anti-infective treatment, comprising:

locating the surface in need of the anti-infective treatment; and contacting the surface in need of the anti-infective coating treatment with an effective amount of a cannabinoidergic-system-acting compound dissolved in an appropriate solvent for inhibiting or reducing gram positive bacterial growth or gram positive bacterial biofilm formation, wherein the cannabinoidergic-system-acting compound comprises (−)-cis-3-[2-Hydroxy-4-(1,1-dimethylheptyl)phenyl]-trans-4-(3-hydroxypropyl)cyclohexanol having a structure of:

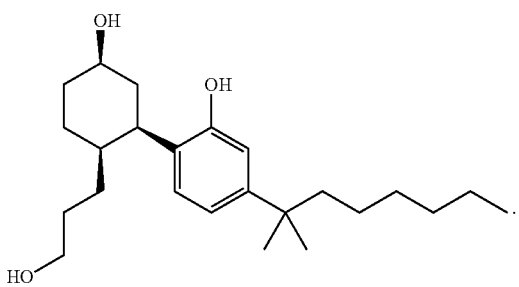 [SMILES: CCCCCCC(C)(C)c1ccc([C@@H]2C[C@H](O)CC[C@@H]2CCCO)c(O)c1]

2. The method of claim 1, wherein the cannabinoidergic-system-acting compound, inhibits or reduces the growth of methicillin-resistant *Staphylococcus aureus* ("MRSA") bacteria on the surface in need of the anti-infective treatment.

3. A method of inhibiting or reducing the growth of gram positive bacteria and gram positive bacterial biofilm on a surface in need of an anti-infective treatment, the method comprising:

locating the surface of the anti-infective treatment; and contacting a cannabinoidergic-system-acting compound dissolved in an appropriate solvent at a concentration of at least about 30 µM with the surface in need of the anti-infective treatment, wherein the cannabinoidergic-system-acting compound is selected from the group consisting of: linoleyl ethanolamide:

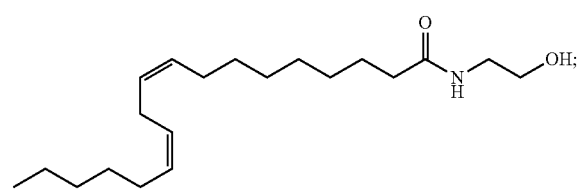 [SMILES: CCCCC/C=C\C/C=C\CCCCCCCC(=O)NCCO]

O-2050:

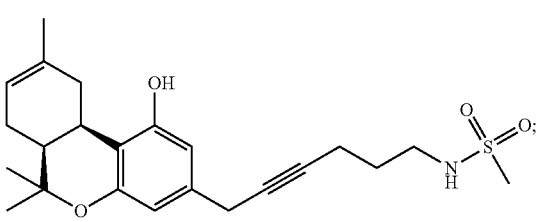 [SMILES: CC1=CC[C@H]2[C@@H](C1)c1c(O)cc(CC#CCCCNS(C)(=O)=O)cc1OC2(C)C]

Noladin ether:

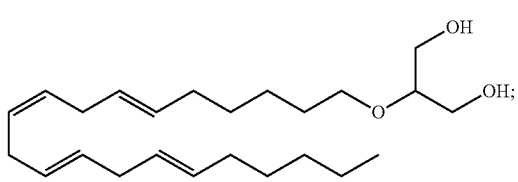 [SMILES: CCCCC/C=C/C/C=C/C/C=C\C/C=C/CCCCCOC(CO)CO]

Anandamide:

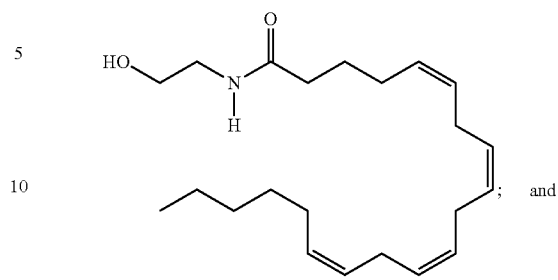

a mixture thereof.

4. The method of claim 3, wherein the surface in need of the anti-infective treatment comprises a medical device surface.

5. The method of claim 4, wherein the medical device surface comprises: a catheter, hemodialysis equipment, a pulmonary ventilator, a heart valve device, dialysis equipment, surgical equipment, a bandage, or a wound dressing material.

6. A method of preventing bacterial biofilm formation caused by *S. epidermidis* on a surface in need of an anti-infective treatment, comprising:

locating the surface in need of the anti-infective treatment; and contacting the surface in need of the anti-infective treatment with an effective amount of a cannabinoidergic-system-acting compound dissolved in an appropriate solvent for inhibiting or reducing gram positive bacterial growth or gram positive bacterial biofilm formation, wherein the cannabinoidergic-system-acting compound comprises (−)-cis-3-[2-Hydroxy-4-(1,1-dimethylheptyl)phenyl]-trans-4-(3-hydroxypropyl)cyclohexanol having a structure of:

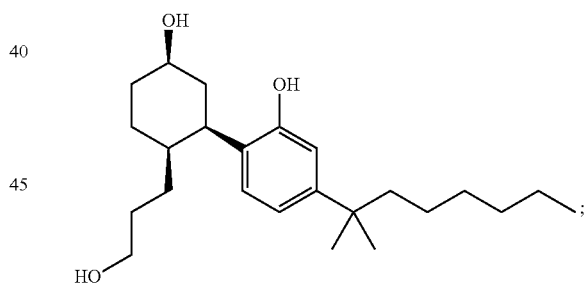

O-2050, having the structure:

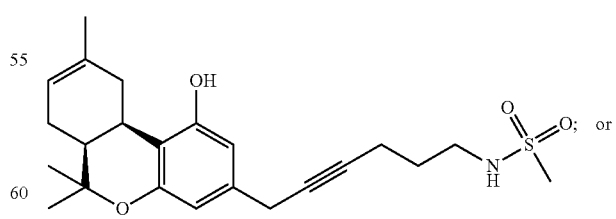

mixtures thereof.

7. A method of inhibiting or reducing the growth of gram positive bacteria and gram positive bacterial biofilm on a surface in need of an anti-infective treatment, the method comprising:

locating the surface in need of the anti-infective treatment; and contacting the surface in need of the anti-infective treatment with an effective amount of a cannabinoidergic-system-acting compound dissolved in an appropriate solvent for inhibiting or reducing gram positive bacterial growth or gram positive bacterial biofilm formation, wherein the cannabinoidergic-system-acting compound is: O-2050:

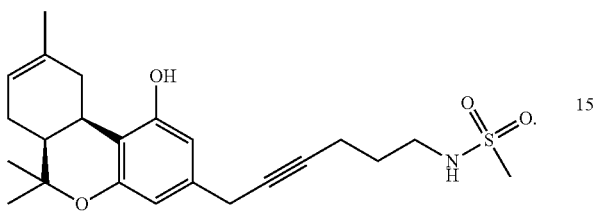

* * * * *